United States Patent [19]

Erpenbach et al.

[11] Patent Number: 5,047,377

[45] Date of Patent: Sep. 10, 1991

[54] PROCESS FOR THE PURIFICATION AND RECOVERY OF THE CONTAMINATED SOLUTION OF THE CATALYST PRODUCED ON CARBONYLATION OF METHANOL AND/OR METHYL ACETATE AND/OR DIMETHYL ETHER

[75] Inventors: Heinz Erpenbach, Cologne; Eitel Goedicke, Bergheim; Winfried Lork, Erftstadt; Heribert Tetzlaff, Frankfurt, all of Fed. Rep. of Germany

[73] Assignee: Hoechst Aktiengesellschaft, Frankfurt am Main, Fed. Rep. of Germany

[21] Appl. No.: 563,396

[22] Filed: Aug. 6, 1990

Related U.S. Application Data

[63] Continuation-in-part of Ser. No. 465,807, Jan. 12, 1990, abandoned.

[30] Foreign Application Priority Data

Jan. 28, 1989 [DE] Fed. Rep. of Germany ....... 3902515

[51] Int. Cl.$^5$ .................. B01J 38/68; B01J 31/40; C07C 67/36; C07C 51/12
[52] U.S. Cl. .................. 502/24; 423/22; 502/22; 502/32; 502/34; 560/232; 562/517; 562/519; 562/891
[58] Field of Search .............. 502/22, 24, 32, 34; 423/22; 560/232; 562/517

[56] References Cited

U.S. PATENT DOCUMENTS

| | | | |
|---|---|---|---|
| 3,969,196 | 7/1976 | Zosel | 502/34 |
| 4,041,082 | 8/1977 | Onoda et al. | 260/604 |
| 4,440,570 | 4/1984 | Erpenbach et al. | 75/121 |
| 4,557,760 | 12/1985 | Erpenbach et al. | 502/22 |
| 4,568,653 | 2/1986 | Schwirten et al. | 502/22 |
| 4,629,711 | 12/1986 | Erpenbach et al. | 502/24 |
| 4,746,640 | 5/1988 | Erpenbach et al. | 502/24 |

FOREIGN PATENT DOCUMENTS

A2054394 7/1980 United Kingdom .

*Primary Examiner*—Paul E. Konopka

[57] ABSTRACT

In a process for the purification and recovery of a contaminated catalyst solution produced during carbonylation of methanol and/or methyl acetate and/or dimethyl ether and containing carbonyl complexes of rhodium, organic and/or inorganic promoters, undistillable organic impurities and acetic acid, acetic anhydride and ethylidene diacetate, the organic impurities and acetic acid, acetic anhydride and ethylidene diacetate are removed from the contaminatd catalyst solution by extraction at pressures from 35 to 450 bar and temperatures from 0° to 120° C. with a liquefied or supercritical gas, and the phase of the liquefied or supercritical gas is separated from the purified, promoter-containing catalyst solution, the phase of the liquefied or supercritical gas is separated by flash vaporization, the recovered gas is re-employed for extraction, acetic acid, acetic anhydride and ethylidene diacetate are separated off from the component which remains liquid, and are combined with the purified catalyst complex to prepare fresh catalyst solution and, finally, the organic impurities remaining as the residue on separation of the phase of the liquefied or supercritical gas is purged.

5 Claims, No Drawings

PROCESS FOR THE PURIFICATION AND RECOVERY OF THE CONTAMINATED SOLUTION OF THE CATALYST PRODUCED ON CARBONYLATION OF METHANOL AND/OR METHYL ACETATE AND/OR DIMETHYL ETHER

CROSS REFERENCE TO RELATED APPLICATION

This is a continuation-in-part application based upon our copending application Ser. No. 07/465,807, filed Jan. 12, 1990, now abandoned.

The invention relates to a process for the purification and recovery of a contaminated catalyst solution produced during carbonylation of methanol and/or methyl acetate and/or dimethyl ether, the contaminated catalyst solution consisting essentially of 1 to 10 % by mass of carbonyl complexes of rhodium, 35 to 80% by mass of quaternary heterocyclic aromatic nitrogen compounds or quaternary organo-phosphorus compounds as organic promoters and/or 35 to 80% by mass of alkali metal salts and, if appropriate, compounds of carbonyl-forming base metals as inorganic promoters, 0,5 to 10 % by mass of undistillable organic impurities and 20to 50% by mass of acetic acid, acetic anhydride and ethylidene diacetate.

For carrying out hydroformylation processes and carbonylation processes, rhodium is used as the noble metal catalyst in the form of diverse complex compounds. Since due to its low availability, rhodium is a very expensive noble metal there are several reports in the literature on the recovery thereof and/or on the purification of rhodium complexes from catalyst systems contaminated with residues and/or distillation bottoms from the abovementioned reactions. EP-A-0,240,703 (=US-A-4,746,640) claims a process which allows the contaminated rhodium-containing catalyst solution obtained on carbonylation of methyl acetate and/or dimethyl ether to be purified in such a way that the undistillable organic residues formed during the reaction are removed from the solution by means of a liquid/liquid extraction with dialkyl ethers and alkanols having in each case 1-4 carbon atoms. The ether phase containing the organic residues is subjected to an after-treatment with iodine and/or methyl iodide, separated off from the remaining catalyst complex which has precipitated and then separated by further distillation into dialkyl ether for re-use and alkanol for re-use as well as acetic acid, acetic anhydride, ethylidene diacetate and undistillable residue. Acetic acid, acetic anhydride and ethylidene diacetate are combined with the purified catalyst phase and with the catalyst complex isolated from the ether phase, freed of the remaining ether and alcohol and fed as fresh catalyst solution to the reaction. Only <0.1% of the rhodium fed to the extraction still remains in the purged residue from the ether phase distillation.

The high price of rhodium permits only its loss-free use as catalyst for large-scale industrial processes. This also applies to the purification and recovery of a contaminated used rhodium catalyst and therefore makes quantitative circulation imperative. This requires a separation, which proceeds without intermediate stages and is as simple as possible, of the organic residue formed in the process from the catalyst solution without any Rh loss and direct re-use of the purified catalyst system in the reaction.

The process of EP-A-0,240,703 (=US-A-4,746,640) fully meets the demands made and, at 99.9%, shows a very good rhodium recovery rate, but it is extremely expensive in the separation train.

The present invention describes a process which avoids this disadvantage and exploits the surprisingly high extraction power of liquefied or supercritical gases for the purification of the contaminated catalyst solution by removal of organic impurities and/or residues. Thus, simple purification of the catalyst solution used in the carbonylation of methanol and/or methyl acetate and/or dimethyl ether and contaminated in the course of the process is possible by extraction preferably with the physiologically acceptable $CO_2$ (carbon dioxide), the separation of the undistillable organic impurities from the catalyst solution taking place without loss of rhodium and without destruction of the catalyst complex and the promoter. The Rh complex and promoter salt can be recycled to the carbonylation process without additional measures. An additional pollution of the environment by waste materials is avoided by the operation with circulation of the inert extractant $CO_2$ used for reprocessing. Only the organic impurities formed in the process are purged and can be disposed of in accordance with the state of the art. The extraction method of the process according to the invention is carried out, depending on the pressure and temperature conditions, in the form of a high-pressure liquid/liquid extraction or of a high-pressure extraction with supercritical gases. A continuous procedure is industrially feasible in any extraction apparatus in which the pressure and temperature can be controlled. Extraction in, for example, a countercurrent column here allows the quantity of extractant to be minimized.

In particular, the process according to the invention comprises removing the organic impurities together with the acetic acid, acetic anhydride and ethylidene diacetate from the contaminated catalyst solution by extraction at pressures from 35 to 450bar and temperatures from 0 to 120° C. with 0,5 to 80parts by weight of liquefied or supercritical gas selected from the group consisting of carbon dioxide, sulfur hexafluoride, dinitrogen monoxide, fluorohydrocarbons, chlorofluorohydrocarbons, bromofluorohydrocarbons. bromochlorofluorohydrocarbons, saturated or unsaturated $C_2$–$C_4$-hydrocarbons, ammonia or mixtures thereof per part by weight of contaminated catalyst solution, and separating the phase of the liquefied or supercritical gas from the purified promoter-containing catalyst solution, separating the phase of the liquefied or supercritical gas by flash vaporization, re-employing the recovered gas for extraction, separating acetic acid, acetic anhydride and ethylidene diacetate from the component which remains liquid and combining it with the purified catalyst complex so as to obtain fresh catalyst solution containing at least 99,90 % of the rhodium contained in the original contaminated catalyst solution, and purging the organic impurities which remain as the residue when the phase of the liquefied or supercritical gas is separated.

Furthermore, the process according to the invention can, preferably and selectively, comprise a) employing 0.5 to 80 and preferably 5 to 20parts by weight of liquefied or supercritical gas, preferably $CO_2$, per part by weight of contaminated catalyst solution, b) additionally adding to the contaminated catalyst solution, together with the liquefied or supercritical gas, 0.03 to 0.4 part by weight of acetic acid and/or acetic anhydride and/or ethylidene diacetate per part by weight of contaminated catalyst solution, c) additionally adding to the contaminated catalyst solution, together with the liquefied or supercritical gas, 0.03 to 0.4 part by weight of methanol per part by weight of contaminated catalyst solution, d) the temperature of the process being maintained between the liquefaction temperature or critical temperature of the gas and 120° C., and e) the pressure of the process being maintained between the liquefaction pressure or critical pressure of the gas and 450bar.

The reaction mixture flowing out of a carbonylation reactor is separated by distillation into the desired end products, especially acetic anhydride and acetic acid, as well as unconverted, circulated starting materials on the one hand and the catalyst solution, obtained as the bottom product and recirculated, on the other hand. A part stream of this catalyst solution which is contaminated in the course of time by undistillable organic products and which, depending on the process conditions, can contain up to 75 M-% (=% by mass) of acetic anhydride, acetic acid and/or ethylidene diacetate, is taken from the catalyst solution circulation and passed t the purification. The catalyst solution contains the noble metal rhodium as a carbonyl complex such as, for example:

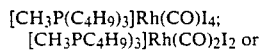

$[C_5H_9N_2]Rh(CO)_2I_2$.

Preferably, the catalyst solution can also contain one or more of the following heterocyclic aromatic nitrogen compounds or organo-phosphorus compounds as organic promoters:

1. N-methylpyridinium iodide, N,N-dimethylimidazolium iodide, N-methyl-3-picolinium iodide, N-methyl-2,4-lutidinium iodide, N-methyl-3,4-lutidinium iodide or N-methyl-quinolinium iodide;

2. tri-n-butyl-methyl-phosphonium iodide, trioctylmethylphosphonium iodide, trilauryl-methyl-phosphonium iodide or triphenyl methyl phosphonium iodide.

Finally, the catalyst solution can contain, as inorganic promoters, alkali metal salts such as, for example, lithium iodide, lithium acetate, potassium iodide or sodium iodide and compounds of the carbonyl-forming base metals Ce, Ti, Zr, Hf, Ge, Sn, Pb, V, Nb, Ta, As, Sb, Bi, Cr, Mo, W, Mn, Re, Fe, Co and Ni.

The purged, contaminated catalyst solution is extracted with the liquefied or supercritical gas, preferably CO,, at 0 to 120° C. (35 to 450 bar). The undistillable organic impurities formed in the reaction and the components acetic anhydride, acetic acid and/or ethylidene diacetate present in the catalyst solution are thus extracted, while the Rh-carbonyl complex with the promoter or promoters remains as the catalyst phase. The $CO_2$ is. recovered from the $CO_2$-containing phase after flashing and, after compression, recycled into the extraction. Acetic anhydride, acetic acid and/or ethylidene diacetate are then redistilled, the undistillable organic impurities being obtained as the residue. The redistilled reaction products are added to the purified catalyst phase (Rh-carbonyl complex and promoter salt) and recycled into the carbonylation process. The undistillable organic impurities are destroyed, for example in an incineration unit.

The process of the invention can be carried out either in continuous operation or discontinues operation.

EXAMPLE 1

For removal of the organic impurities, 400 g of catalyst solution of the composition 6.1 M-% of rhodium carbonyl complex $[CH_3P(C_4H_9)_3][Rh(CO)_2I_2](-4.0$ g $=1.0$ M-% of Rh), 67.5 M-% of methyl-tri-n-butylphosphonium iodide, 2.75 M-% of organic impurities and 23.65 M-% of a mixture of acetic acid, acetic anhydride and ethylidene diacetate are taken from the catalyst circulation of the methanol/ methyl acetate carbonylation and extracted at 80° C. and 300 bar with 2,900 g of $CO_2$. The $CO_2$ phase is separated from the catalyst phase and, after flashing to a pressure of 50 bar at 16° C., separated into $CO_2$ and 104.5 g of extract. After compression and temperature adjustment to the extraction conditions, the $CO_2$ is re-employed for extraction, while the extract is separated by distillation into 94.6 g of acetic acid/acetic anhydride/ ethylidene diacetate mixture and 9.9 g of undistillable organic impurities as a tarry residue (Rh content 0.04 M-%). The recovered mixture of acetic acid, acetic anhydride and ethylidene diacetate is combined with the refined catalyst phase and added again as 390.1 g of purified catalyst solution having an Rh content of 4 g to the catalyst circulation. The recycle rate of the rhodium into the carbonylation process is 99.90% liter the purification of the contaminated catalyst solution taken off.

EXAMPLE 2

For removing the organic impurities, 400 g of catalyst solution of the composition 4.9 M-% of rhodium carbonyl complex $[Li][Rh(CO)_2I_2](\doteq4.8$ g $=1.2$ M-% of Rh), 49.1 M-% of lithium iodide, 4.0 M-% of organic impurities and 42.0 M-% of a mixture of acetic acid, acetic anhydride and ethylidene diacetate are taken from the catalyst circulation of the methanol/methyl acetate carbonylation and extracted at 40° C. and 100 bar with 3,200 g of $CO_2$. The $CO_2$ phase is separated from the catalyst phase and, after flashing to a pressure of 50 bar at 16° C., separated into $CO_2$ and 182.1 g of extract. After compression and adjustment of the temperature to the extraction conditions, the $CO_2$ is re-employed for extraction, while the extract is separated by distillation into 168 g of acetic acid/ acetic anhydride/ethylidene diacetate mixture and 14.1 g of undistillable organic impurities as a tarry residue (Rh content 0.03 M-%). The recovered mixture of acetic acid, acetic anhydride and ethylidene diacetate is combined with the refined catalyst phase and added again as 385.9 g of purified catalyst solution having an Rh content of 4.8 g to the catalyst circulation. The recycle rate of the rhodium into the carbonylation process is 99.91% after the purification of the contaminated catalyst solution taken off.

EXAMPLE 3

For removal of the organic impurities, 400 g of catalyst solution of the composition 6.05 M-% of rhodium carbonyl complex $[C_5H_9N_2][Rh(CO)_2I_2](\doteq4.88$ g $\doteq1.22$ M-% of Rh), 45.35 M-% of N,N-dimethylimidazolium iodide, 3.5 M-% of organic impurities and 45.1 M-% of a mixture of acetic acid, acetic anhydride and ethylidene diacetate are taken from the catalyst circulation of the carbonylation of dimethyl ether and extracted at 60° C. and 150 bar with 2,800 g of $CO_2$ with the addition of 300 g of a mixture of acetic acid, acetic anhydride and ethylidene diacetate. The $CO_2$ phase is separated from the catalyst phase and, after flashing to a pressure of 35 bar at 16° C., separated into $CO_2$ and 311.5 g of extract. After compression and adjustment of the temperature to the extraction conditions, the $CO_2$ is re-employed for extraction, while the extract is separated by distillation into 300 g cf acetic acid/acetic anhydride/ethylidene diacetate mixture and 11.5 g of undistillable organic impurities as a tarry residue (Rh content 0.03 M-%). The recovered mixture of acetic acid, acetic anhydride and ethylidene diacetate is re-employed for extraction, while the raffinate as 388.5 g of purified catalyst solution having an Rh content of 4.88 g is added again to the catalyst circulation. The recycle rate of the rhodium into the carbonylation process is 99.93% after the purification of the contaminated catalyst solution taken off.

EXAMPLE 4

For removing the organic impurities, 400 g of catalyst solution of the composition 3.99 M-% of rhodium carbonyl complex $[CH_3P(C_4H_9)_3][Rh(CO)I_4]$ ($\hat{=}$1.92 g $\hat{=}$0.48 M-% of Rh), 64.9 M-% of methyl-tri-n-butylphosphonium iodide, 3.2 M-% of organic impurities and 27.91 M-% of a mixture of acetic acid, acetic anhydride and ethylidene diacetate are taken from the catalyst circulation of the methanol/ methyl acetate carbonylation and extracted at 25° C. and 70 bar with 2,500 g of $CO_2$ with 250 g of added methanol. The $CO_2$ phase is separated from the catalyst phase and, after flashing to a pressure of 50 bar at 25° C., separated into $CO_2$ and 260.4 g of extract. After compression and adjustment of the temperature to the extraction conditions, the $CO_2$ is re-employed for extraction, while the extract is separated by distillation into 250.0 g of acetic acid/ acetic anhydride/ethylidene diacetate/methanol mixture and 10.4 g of undistillable organic impurities as a tarry residue (Rh content 0.015 M-%). The recovered mixture of acetic acid, acetic anhydride, ethylidene diacetate and methanol is combined with the refined catalyst phase and added again as 639.6 g of purified catalyst solution having an Rh content of 1.92 g to the catalyst circulation. The recycle rate of the rhodium into the carbonylation process is 99.92% after the purification of the contaminated catalyst solution taken off. The methanol employed in the extraction does not have to be removed from the catalyst solution, since it is converted in the carbonylation reactor to the desired reaction products acetic acid and acetic anhydride.

EXAMPLE 5

For removing the organic impurities, 400 g of catalyst solution of the composition 6.05 M-% of rhodium carbonyl complex $[C_5H_9N_2][Rh(CO)_2I_2]$ ($\hat{=}$4.88 g $\hat{=}$1.22 M-% of Rh), 45.35 M-% of N,N-dimethylimidazolium iodide, 3.5 M-% of organic impurities and 45.1 M-% of a mixture of acetic acid, acetic anhydride and ethylidene diacetate are taken from the catalyst circulation of the carbonylation of dimethyl ether and extracted at 40° C. and 300 bar with 4,000 g of ethylene with 300 g of an added mixture of acetic acid, acetic anhydride and ethylidene diacetate. The ethylene phase is separated from the catalyst phase and, after flashing to a pressure of 50 bar at 5° C., separated into ethylene and 311.6 g of extract. After compression and adjustment of the temperature to the extraction conditions, the ethylene is re-employed for extraction, while the extract is separated by distillation into 300 g of acetic acid/acetic anhydride/ethylene diacetate mixture and 11.6 g of undistillable organic impurities as a tarry residue (Rh content 0.02 M-%). The recovered mixture of acetic acid, acetic anhydride and ethylidene diacetate is re-used for extraction, while the raffinate as 388.4 g of purified catalyst solution having an Rh content of 4.88 g is added again to the catalyst circulation. Rhodium recycle rate: 99.95%.

EXAMPLE 6

For removing the organic impurities, 400 g of catalyst solution of the composition 3.99 M-% of rhodium carbonyl complex $[CH_3P(C_4H_9)_3][Rh(CO)I_4]$ ($\hat{=}$1.92 g $\hat{=}$0.48 M-% of Rh), 64.9 M-% of methyl-tri-n-butylphosphonium iodide, 3.2 M-% of organic impurities and 27.91 M-% of a mixture of acetic acid, acetic anhydride and ethylidene diacetate are taken from the catalyst circulation of the methanol/ methyl acetate carbonylation and extracted at 50° C. and 150 bar with 2,500 g of ®Frigen 23 ($CHF_3$) with 300 g of added methanol. The ®Frigen 23 phase is separated from the catalyst phase and, after flashing at 1 bar and 19° C., separated into ®Frigen 23 and 310.2 g of extract. After compression and adjustment of the temperature to the extraction conditions, the ®Frigen 23 is re-employed for extraction, while the extract is separated by distillation into 300 g of acetic acid/acetic anhydride/ethylidene diacetate/methanol mixture and 10.2 g of undistillable organic impurities as a tarry residue (Rh content 0.018 M-%). The recovered mixture of acetic acid, acetic anhydride, ethylidene diacetate and methanol is combined with the refined catalyst phase and added again as 689.8 g of purified solution having an Rh content of 1.92 g to the catalyst circulation. Rhodium recycle rate: 99.90%.

We claim:

1. A process for the purification and recovery of a contaminated catalyst solution produced during carbonylation of at least one substance selected from methanol, methyl acetate and dimethyl ether, the contaminated catalyst solution consisting essentially of 1 to 10 % by mass of carbonyl complexes of rhodium, 35 to 80% by mass of quaternary heterocyclic aromatic nitrogen compounds or quaternary organo-phosphorus compounds as organic promoters, or 35 to 80% by mass of alkali metal salts or compounds of carbonyl-forming base metals as inorganic promoters, 0.5 to 10 % by mass of undistillable organic impurities and 20 to 50% by mass of acetic acid, acetic anhydride and ethylidene diacetate the process comprising removing the organic impurities together with the acetic acid, acetic anhydride and ethylidene diacetate from the contaminated catalyst solution by extraction at pressures from 35 to 450 bar and temperatures from 0 to 120° C. with 0.5 to 80 parts by weight of liquefied or supercritical gas selected from the group consisting of carton dioxide sulfur hexafluoride dinitrogen monoxide, fluorohydrocarbon, chlorofluorohydrocarbons, bromofluorohydrocarbons, bromochlorofluorohydrocarbons, saturated or unsaturated $C_2$- to $C_4$-hydrocarbons, ammonia or mixtures thereof per part by weight of contaminated catalyst solution, and separating the phase of the liquefied or supercritical gas from the purified promoter-containing catalyst solution, separating the phase of the liquefied or supercritical gas by flash vaporization, re-employing the recovered gas for extraction, separating acetic acid, acetic anhydride end ethylidene diacetate from the component which remains liquid and combining it with the purified catalyst complex so as to obtain fresh catalyst solution containing at least 99.90% of the rhodium contained in the original contaminated catalyst solution, and purging the organic impurities which remain as the residue when the phase of the liquefied or supercritical gas is separated.

2. A process as claimed in claim 1, additionally comprising adding to the contaminated catalyst solution, together with the liquefied or supercritical gas, 0.03 to 0.4 parts by weight of at least one substance selected from acetic acid, acetic anhydride, or ethylidene diacetate per part by weight of contaminated catalyst solution.

3. A process as claimed in claim 1, additionally comprising adding to the contaminated catalyst solution, together with the liquefied or supercritical gas, 0.03 to 0.4 parts by weight of methanol per part by weight of contaminated catalyst solution.

4. A process as claimed in claim 1, wherein the temperature of the process is maintained between the liquefaction temperature or critical temperature of the gas and 120° C.

5. A process as claimed in claim 1, wherein the pressure of the process is maintained between the liquefaction pressure or critical pressure of the gas and 450bar.

* * * * *